US005202521A

United States Patent [19]

Brown et al.

[11] Patent Number: 5,202,521

[45] Date of Patent: Apr. 13, 1993

[54] MONOOLEFIN/PARAFFIN SEPARATION BY SELECTIVE ABSORPTION

[75] Inventors: Ronald E. Brown; Robert L. Hair, both of Bartlesville, Okla.

[73] Assignee: Phillips Petroleum Company, Bartlesville, Okla.

[21] Appl. No.: 893,630

[22] Filed: Jun. 5, 1992

[51] Int. Cl.$^5$ ........................ C07C 7/148; C07C 7/17; B01D 3/00; B01D 47/00

[52] U.S. Cl. .................................... 585/848; 585/845; 585/856; 585/864; 203/84; 423/245.1; 55/84

[58] Field of Search ............... 585/845, 848, 856, 864; 203/84; 423/245.1; 55/84

[56] References Cited

U.S. PATENT DOCUMENTS

| | | | |
|---|---|---|---|
| 3,260,766 | 7/1966 | Nudenberg et al. | 260/677 |
| 3,401,117 | 9/1968 | Dunlop et al. | 208/308 |
| 4,025,574 | 5/1977 | Tabler et al. | 260/677 A |
| 4,053,369 | 10/1977 | Cines | 203/52 |
| 4,398,052 | 8/1983 | Tabler et al. | 585/845 |
| 4,400,564 | 8/1983 | Johnson et al. | 585/845 |
| 4,504,692 | 3/1985 | Arakawa et al. | 585/617 |
| 4,639,308 | 1/1987 | Lee | 208/100 |

*Primary Examiner*—Anthony McFarlane
*Assistant Examiner*—Nhat Phan
*Attorney, Agent, or Firm*—K. K. Brandes

[57] ABSTRACT

A selective absorption process for separating $C_2$–$C_4$ alkenes (in particular ethylene) from $C_1$–$C_5$ alkanes with a liquid extractant comprising dissolved copper(I) compound(s), in particular dissolved Cu(I) hydrocarbonsulfonate(s), is carried out in a one-column operation, wherein an overhead product is withdrawn which contains alkene(s) at a lower concentration than the feed, a side product is withdrawn which contains alkene(s) at a higher concentration than the feed, and a bottoms stream is withdrawn which contains primarily the liquid extractant.

11 Claims, 2 Drawing Sheets

MONOOLEFIN/PARAFFIN SEPARATION BY SELECTIVE ABSORPTION

BACKGROUND OF THE INVENTION

This invention relates to the recovery of $C_2$–$C_4$ monoolefins from fluid comprising monoolefins and paraffins by selective absorption employing a dissolved copper(I) complexing agent as extractant.

The separation of monoolefins from paraffins by means of dissolved copper(I) complexing agents, e.g., (copper(I) sulfonates or carboxylates, is known and has been described in U.S. Pat. Nos. 4,025,574 and 4,639,308. Generally, the feed gas is contacted with an absorbing solution which contains the copper(I) complexing solution, and the absorbed monoolefin is recovered from the absorbing solution by desorption in a separate "stripper" unit. The present invention is directed to an improved process for separating $C_2$–$C_4$ monoolefins for paraffins in a continuous, one-column operation.

SUMMARY OF THE INVENTION

It is an object of this invention to separate $C_2$–$C_4$ monoolefins from paraffins by selective absorption employing dissolved copper(I) complexing agent(s) as extractant. It is another object of this invention to employ dissolved copper(I) hydrocarbonsulfonate(s) as extractant. It is a further object of this invention to recover high purity ethylene. Other objects and advantages will be apparent from the detailed description and the appended claims.

In accordance with this invention, a process for separating light alkenes from light alkanes comprises:

(1) contacting in an absorption column a fluid feed stream comprising at least one alkene containing 2–4 carbon atoms per molecule and at least one alkane containing 1–5 carbon atoms per molecule with at least one liquid extractant selected from the group consisting of dissolved copper(I) hydrocarbonsulfonates, dissolved copper(I) hydrocarbonphosphates and dissolved copper(I) carboxylates, wherein said at least one liquid extractant is introduced into said absorption column at an entry located above the entry point of said fluid feed;

(2) withdrawing a gaseous overhead product stream in which the concentration of said at least one alkene is less than in said fluid feed, wherein said overhead product stream is withdrawn at an exit point located above the entry point of said at least one extractant;

(3) withdrawing a gaseous side product stream in which the concentration of said at least one alkene is higher than in said fluid feed stream, wherein said side product stream is withdrawn at an exit point located below the entry point of said fluid stream; and (4) withdrawing a liquid bottoms stream comprising (preferably consisting essentially of) said at least one liquid extractant, at an exit point located below the exit point of said side stream.

DETAILED DESCRIPTION OF THE INVENTION

Figure 1:
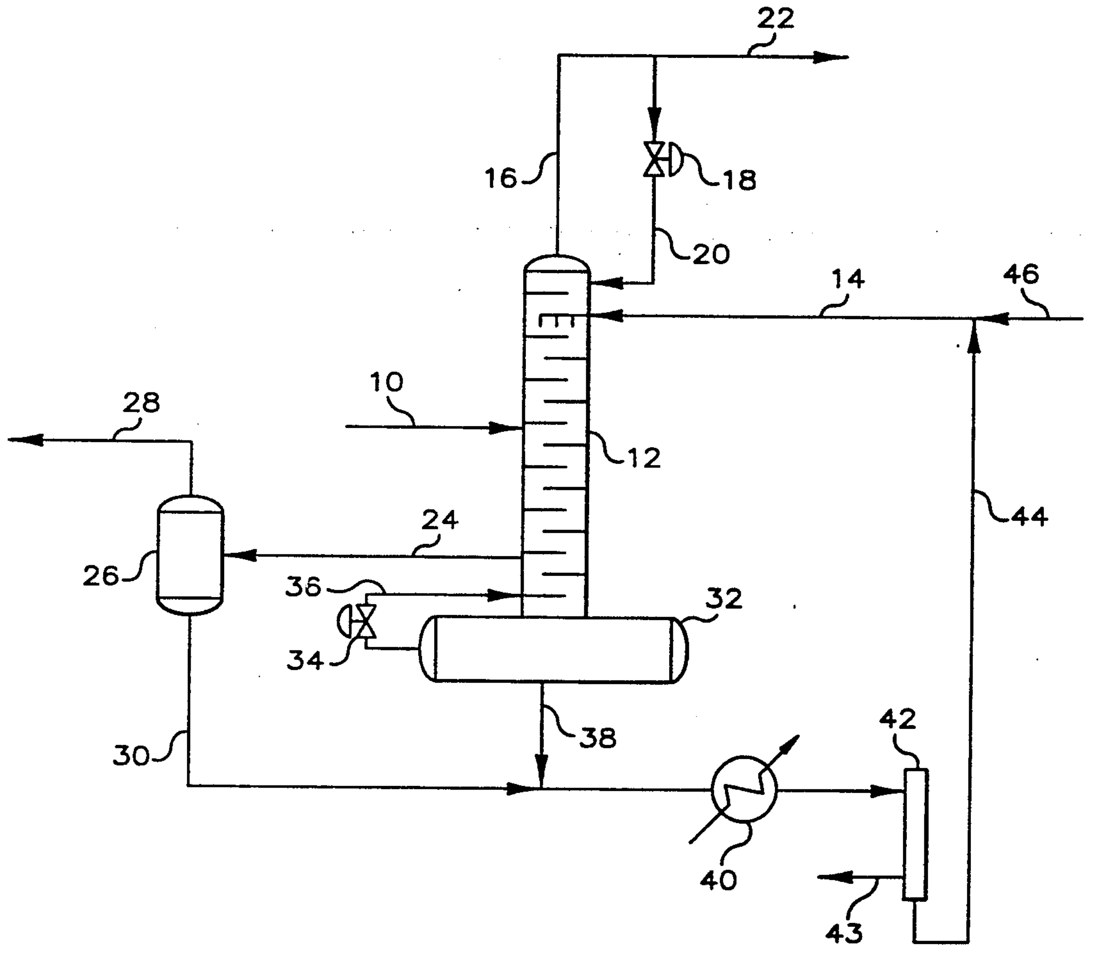
FIG. 1 illustrates a preferred embodiment of the selective absorption process of this invention for separating $C_2$–$C_4$ alkene(s) from $C_1$–$C_5$ alkane(s) employing a single column.

Any suitable fluid (preferably gaseous) which contains $C_2$–$C_4$ alkene(s) and $C_1$–$C_5$ alkane(s), can be employed as the feed in the separation process of this invention. Generally, the volume percentage of alkene(s) in the feed is in the range of about 1 to about 75 volume-%, and preferably is about 1–50 volume-%. Generally, the volume percentage of alkane(s) in the feed is in the range of about 25 to about 99 volume-%, and preferably is about 50–99 volume-%.

Feed monoolefins (alkenes) can be ethylene (presently preferred), propylene, butene-1, butene-2, isobutylene and mixtures thereof. Preferred feed paraffins (alkanes) include methane, ethane, propane, butane, isobutane and mixtures thereof. Other feed components may also be present as long as they do not adversely affect the separation process (e.g., by significant complex formation with the Cu(I) extractants). These optional components can be hydrogen gas (generally present in trace amounts, such as less than about 0.1 volume-% $H_2$, up to about 50 volume-% $H_2$), nitrogen gas (generally present in trace amounts, such as less than about 0.1 volume-% $N_2$, up to about 10 volume-%, $N_2$) and carbon dioxide (generally present in trace amounts, such as less than about 0.1 volume-% $CO_2$, up to about 5 volume-% $CO_2$). Other compounds which may also be present as fed components in minute amounts (less than about 0.1 volume-% each) include carbon monoxide, hydrogen sulfide, mercaptans and the like. A particularly suitable fluid feed is an off-gas from a catalytic FCC cracker, as is described in Table I of U.S. Pat. No. 4,639,308.

Any suitable dissolved copper(I) salt of a hydrocarbonsulfonic acid, also referred to as copper(I) hydrocarbonsulfonates, can be employed as the entrainer in the process of this invention. Preferred copper(I) salts of hydrocarbonsulfonates are disclosed in U.S. Pat. No. 4,025,579 and include Cu(I) salts of alkanesulfonic acids which may be straight chain or branched containing 4–20 carbon atoms per molecule, and Cu(I) salts of aromatic sulfonic acids containing 6–22 carbon atoms per molecule. Non-limiting examples of suitable Cu(I) salts of alkanesulfonic acids include Cu(I) salts of n-butanesulfonic acid, of 2-ethyl-1-hexanesulfonic acid, of 2-methylnonanesulfonic acid, of dodecanesulfonic acid, 2-ethyl-5-n-octyldecanesulfonic acid, of n-eicosanesulfonic acid, and mixtures thereof. Non-limiting examples of Cu(I) salts of aromatic sulfonic acids useful in the practice of this invention include Cu(I) salts of benzenesulfonic acid, alkylbenezenesulfonic acids wherein the alkyl member contains from 1 to 10 carbon atoms, such as p-toluenesulfonic acid, p-dodecylbenzenesulfonic acid, p-hexadecylbenzenesulfonic acid, and the like, naphthalenesulfonic acid and mixtures thereof. A presently preferred Cu(I) salt of an aromatic sulfonic acid is the Cu(I) salt of p-dodecylbenzenesulfonic acid. Cu(I) salts of petroleum sulfonic acids which comprise Cu(I) salts of various alkane sulfonic acids and aromatic sulfonic acids can also be used in the practice of this invention. Such petroleum sulfonic acids can be prepared by sulfonation, generally with an $SO_3/SO_2$ mixture, of a deasphalted solvent-refined petroleum fraction having a viscosity of about 140–720 SUS at 210° F.

Any suitable dissolved copper (I) salt of a dialkylphosphoric acid, also referred to as copper(I) dialkylphosphate, can be employed as the extractant. Generally, each alkyl group of the dialkylphosphate contains 1-12 carbon atoms. Preferred copper(I) salts of dialkylphosphoric are disclosed in U.S. Pat. No. 4,025,574. The Cu(I) dialkylphosphates useful in the practice of this invention include Cu(I) dimethylphosphate, Cu(I) diethylphosphate, Cu(I) di-n-butylphosphate, Cu(I) di-2-ethylhexylphosphate, Cu(I) di-n-dodecylphosphate and mixtures thereof.

Any suitable dissolved copper(I) salt of a carboxylic acid, also referred to as copper(I) carboxylate, can be employed as the extractant. The carboxylic acid from which the Cu(I) carboxylate is prepared can be an aliphatic carboxylic acid, a cycloaliphatic carboxylic acid or an aromatic carboxylic acid and generally contains 1-15 carbon atoms per molecule. The Cu(I) carboxylate can contain 1 or 2 or more than 2 carboxylates (COO−) groups. Non-limiting examples of suitable Cu(I) carboxylates include Cu(I) formate, Cu(I) acetate, copper(I) propionate, copper(I) hexaneoates, copper(I) octanoates, copper decanoates, and mixtures thereof.

The above-described copper(I) salts are dissolved in at least one aliphatic or cycloaliphatic or aromatic hydrocarbon solvent, preferably containing 6-15 carbon atoms per molecule to produce a solution of the Cu(I) salt. Examples of suitable solvents are n-hexane, n-octane, n-decane, cyclohexane, cyclopentane, benzene, toluene, xylene isomers, ethylbenzene, isopropylbenzene, 1,3,5-trimethylbenzene, hexamethylbenzene, polynucleararomatic hydrocarbons such as naphthalene, methylnaphthalenes and the like. It is also possible to employ mixtures of the above hydrocarbons, such as light cycle oil, and the like. Aromatic solvents are presently preferred. Xylene(s), i.e., ortho- or meta- or para-xylene or a mixture of two or three xylenes (at any suitable ratio), are particularly preferred. Generally, the concentration of the dissolved copper(I) salt in the liquid extractant is about 0.05-2 mol/l, preferably about 0.2-1.5 mole/l. Any suitable weight ratio of dissolved Cu(I) salt(s) contained in the liquid extractant to the gaseous feed can be employed in step (1). This weight ratio generally is in the range of about 0.02:1 to about 10:1, preferably in the range of about 1:1 to about 2:1.

Any suitable total column height, packed column height, column diameter and number of trays in the absorption column can be employed. The exact dimensions and column designs depend on the scale of the operation, the exact feed composition, the exact extractant composition, the desired recovery and degree of purity of the various product, and the like, and can be determined by those having ordinary skills in the art. A column containing about 30-50 trays (preferably about 38-42 trays) and a spacing of about 1-3 feed (preferably about 1.8-2.2 feet) between trays is estimated to be a feasible arrangement in a commercial operation.

Any suitable feed entry location can be selected. Generally, the feed entry location is in the range of from about 30 to about 80 percent of the total height of the packed or trayed column, upward from the bottom of the column, preferably in the range of from about 40 to about 70 percent.

Any suitable extractant entry location can be selected. Generally, the extractant entry location is in the range of from about 50 to about 99 percent of the total height of the packed or trayed column (i.e., within the upper half of the column), preferably in the range of from about 70 to about 99 percent.

Any suitable side product exit location can be selected. Generally, the exit point of the gaseous (vaporized) side product (which contains a higher concentration of alkene(s) than the feed) is in the range of about 2 to about 50 percent of the total height of the column (i.e., within the lower half of column), preferably in the range of about 5 to about 30 percent. The gaseous side product is generally cooled so as to condense small amounts of entrained extractant solvent vapor. The condensed solvent is combined with the extractant bottom stream (described below).

The exit point of the gaseous (vaporized) overhead product is at or near the top of the column. Optionally, a portion of the overhead product may be condensed and returned as reflux to the column (at a point above the entry point of the liquid extractant). If a portion of the overhead stream is refluxed, any suitable reflux ratio (i.e., the weight ratio of the portion of condensed overhead vapor which is returned to the absorption column to the portion of condensed overhead vapor which is withdrawn as overhead product) can be employed in the selective absorption process of this invention. Generally, the reflux ratio is in the range of about 0:1 to about 5:1, preferably about 0:1 to about 2:1.

The exit point of the extractant is at or near the bottom of the column. Generally, a portion of this bottom stream is heated by an external heat source and returned to the column at a point below the exit point of the gaseous side product. Generally, about 5-20 percent of the extractant which is withdrawn at the bottom of the column is returned (after having been heated) to the column (as a so-called reboiler stream). The portion of the extractant which is not returned as the reboiler stream is generally cooled and filtered (in any order) and is reintroduced, optionally with additional fresh extractant, to the column at the extractant entry point.

Any suitable pressure and temperature conditions in the absorption column can be employed. Generally, the temperature is about 50°-200° F. in the upper portion of the column and about 200°-400° F. in the lower portion of the column. The pressure is generally in the range of about 5-30 psig throughout the column.

The invention can be better understood by reference to the figures and the following description of preferred embodiments of the invention. The following examples are presented to further illustrate the invention and are not intended to unduly limit the scope of this invention.

EXAMPLE I

This example illustrates a preferred operational mode of this invention employing a monoolefin/paraffin feed gas. As shown in FIG. 1, the feed gas is introduced through conduit 10 into a trayed absorption column 12. The liquid extractant (preferably a solution of copper(I) dodecylbenzenesulfonate in a xylene solvent) is introduced through conduit 14 into the distillation column. The overhead stream is withdrawn through conduit 16. Optionally, a portion of the overhead stream is returned as reflux through control valve 18 and conduit 20 to the absorption column. The gaseous overhead product which contains primarily the paraffin(s) is withdrawn through conduit 22.

A side stream containing primarily the monoolefin(s) and a small amount of vaporized xylene solvent is withdrawn through conduit 24. This gaseous side stream is cooled in separator vessel 26 so as to condense xylene and to obtain a purer gaseous side product 28 (which consists primarily of the monoolefin) and xylene solvent stream 30. The bottoms product consisting primarily of the extractant is collected in kettle 32 which is generally externally heated. A portion of the heated bottoms product is returned to the absorption column through control valve 34 and conduit 36. The major portion of the bottoms product (which consists essentially of the extractant) is withdrawn through conduit 38 and combined with solvent stream 30, cooled by means of heat exchanger 40 and pumped through filter 42. Retained solids (43) are removed when necessary. The filtered extractant stream 44, optionally combined with make-up stream 46 containing fresh extractant, is introduced through conduit 14 into the absorption column. Pumps, conventional process control equipment and gauges are not shown in FIG. 1.

EXAMPLE II

This example further illustrates the separation process of this invention. In a pilot plant test using the above-described equipment, a feed gas containing 20 volume-% ethylene and 80 volume-% ethane was introduced into an absorption column 12 (height: 4.5 feet; inner diameter: 2 inches; containing ten trays) through conduit 10 at a rate of 300 cc/minute. A 0.4 molar solution of copper(I) dodecylbenzenesulfonate in xylene was introduced as the extractant into the absorption column 12 through conduit 14 at a rate of 300 cc/hour. The flow rate of the overhead stream 16, which contained about 5.5 volume-% ethylene and about 94.5 volume-% ethane, was about 252 cc/minute. The side product stream 28, which contained about 96 volume-% ethylene and about 4 volume-% ethane, was withdrawn at a rate of about 48 cc/minute. Thus, about 77% of the feed ethylene had been recovered ($0.96\times48\times100$ divided by $0.20\times300$). The temperature profile in the absorption column was approximately as follows: 80° F. at the entrance of point of the extractant, 100° F. at the entrance point of the feed gas, 310° F. at the exit point of the side product stream, and 321° F. at the exit point of the bottoms product. The pressure in the absorption column was about 11 psig.

In a control test which also employed a 20/80 ethylene/ethane feed gas (feed rate: 400 cc/minute) and a 0.4 molar Cu(I) solution (feed rate: 300 cc/hour) but used a conventional setup comprising an absorption column (operated at about 80° F. and 10 psig) and a separate stripper/desorption column (operated at a kettle temperature of 300° F. and 12 psig), the product gas stream contained only about 63% ethylene (was compared to 96% in the above-described one-column operation in accordance with this invention), whereas the ethylene recovery was about 74% (i.e., approximately the same as in the above-described one-column operation in accordance with this invention). Thus, the selective absorption process of this invention unexpectedly achieved a significantly higher alkene purity of the product than the conventional two-column absorption/stripper operation, at a comparable alkene recovery.

EXAMPLE III

This example illustrates the recovery of ethylene from a gas mixture containing 30.7 volume-% ethylene, 33.6 volume-% ethane and 35.7 volume-% methane (so as to simulate a catalytic cracker off-gas) in accordance with this invention. The test procedure was essentially the same as described in the first paragraph of Example II, except that the feed gas rate was 214 cc/minute and the rate of the 0.4 molar solution of Cu(I) dodecylbenzenesulfonate in xylene was 800 cc/hour. Test results were as follows: the side product stream 28 contained 98% volume-% ethylene and was withdrawn at a rate of 63.6 cc/minute; and the overhead product contained 2.2 volume-% ethylene, 47.0 volume-% ethane and 50.8 volume-% methane and was withdrawn at a rate of 150.4 cc/minute. The ethylene recovery was about 95%.

EXAMPLE IV

Figure 2:
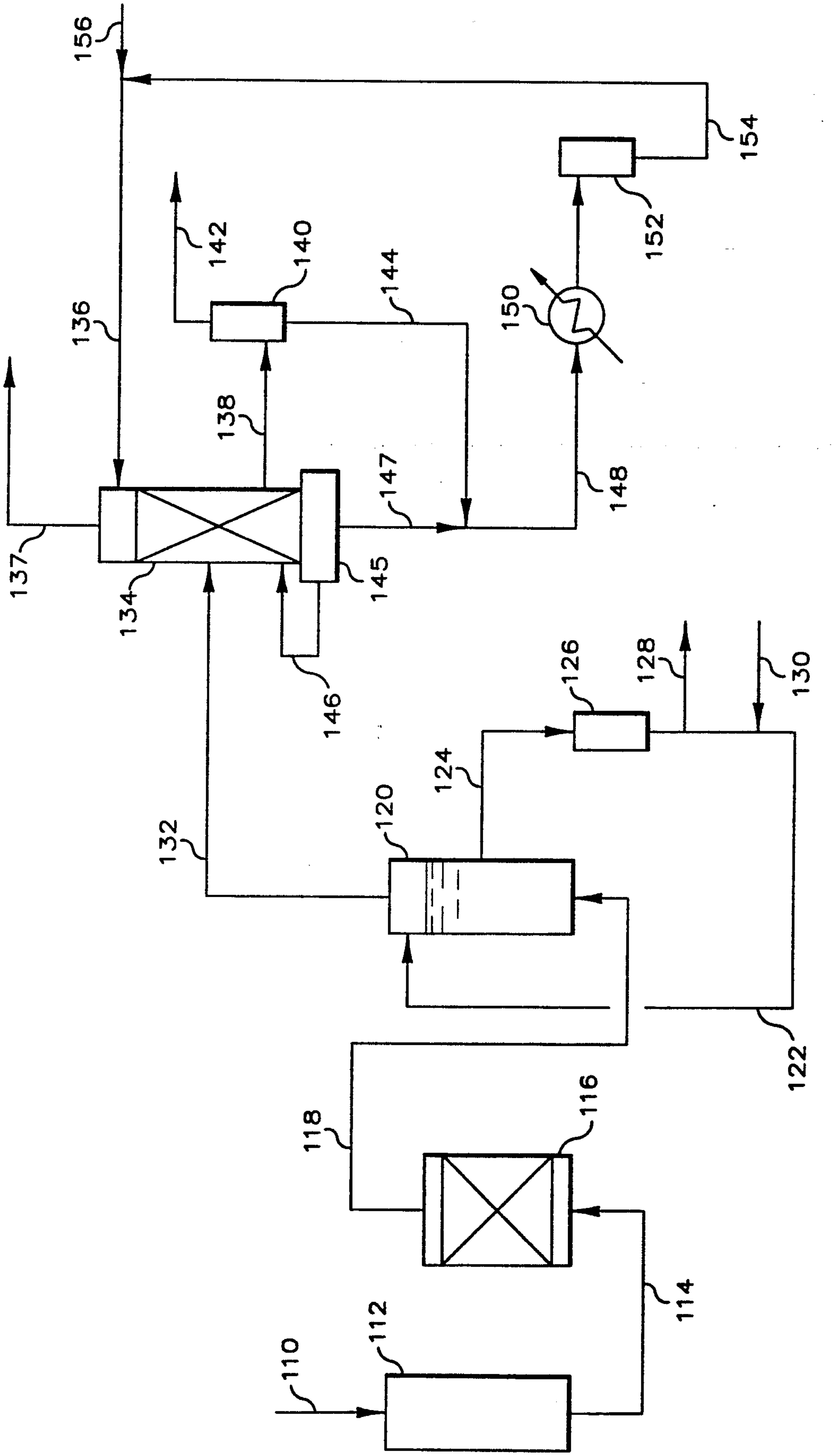
FIG. 2 illustrates the recovery of $C_2$–$C_4$ alkene(s) from a catalytic cracker off-gas by the selective absorption process of this invention employing a single column.

This example illustrates the removal of $C_2$–$C_4$ alkene(s) from a catalytic cracker off-gas. Referring to FIG. 2, cracker off-gas stream 110 containing primarily hydrogen gas, $C_1$–$C_4$ alkanes and $C_2$–$C_4$ alkenes (in particular ethylene) is introduced into a caustic treater 112, in which acidic gases (such as $H_2S$ and $CO_2$) are removed by means of an aqueous alkali metal hydroxide solution. The thus-treated gas stream 114 is dried in dryer unit 116 containing an effective desiccant (such as a molecular sieve zeolite). Dried gas stream 118 is sparged through a solution of a copper(I) hydrocarbonsulfonate (in particular Cu(I) dodecylbenzenesulfonate in xylene) contained in absorber vessel 120 so as to remove small amounts of impurities, such as carbon monoxide, mercaptans, organic sulfides and acetylene.

In a continuous operation, the Cu(I) hydrocarbonsulfonate absorbing solution is added through conduit 122, and used absorbing solution is withdrawn at an equal rate through conduit 124. The used absorbing solution is pumped through filter 126 (where small amounts of suspended solids, such as copper oxide or sulfide, are removed). A portion of the filtered, used absorbing solution is withdrawn through conduit 128 and is replaced with an equal amount of fresh absorbing solution through conduit 130. The combined absorbing solution is then introduced into the absorber vessel through conduit 122, as described above.

The purified gas stream 132 is introduced into a selective absorption column 134 (in accordance with this invention). An extractant solution of an effective Cu(I) hydrocarbonsulfonate (preferably a 0.4 molar solution of Cu(I) dodecylbenzenesulfonate xylene) is introduced through conduit 136 into the upper portion of the absorption column. A gaseous side stream 138 containing mainly alkene(s), in particular ethylene, and some entrained solvent (xylene) vapor is introduced into a cooled separator vessel 140 where the side stream is separated into a gaseous alkene product stream 142 and a condensed solvent stream 144. A portion of the bottoms product which has accumulated in heated kettle 145 is recycled as a reboiler stream 146 to column 134. The nonrecycled portion of the bottoms product (containing mainly the extractant solution) 147 is combined with solvent stream 144 (from separator vessel 140) to form a combined extractant stream 148, which is cooled in heat exchanger 150 and then filtered by means of filter 152. The filtered extractant stream 154 and a make-up stream of fresh extractant 156 are combined. The combined extractant stream 136 is introduced into the absorption column 134, as described above. Filters 126 and 152 can be cleaned as needed, either by replacing the filter screens or by back-flushing. In order to continue the continuous operation described above, generally two parallel filters 126 and two parallel filters 152 are installed, so that one filter 126 and/or one filter 152 can be used to filter the appropriate liquid stream while the second parallel filter 126 or 152 is being cleaned.

Reasonable variations, modifications and adaptations for various usages and conditions can be made within the scope of the disclosure and the appended claims, without departing from the scope of this invention.

That which is claimed is:

1. A process for separating ethylene from light alkanes which comprises:

(1) contacting in an absorption column a gaseous feed stream comprising ethylene and at least one alkane selected from the group consisting of methane, ethane, propane, butane and isobutane with at least one liquid extractant selected from the group consisting of dissolved copper(I) hydrocarbonsulfonates, wherein said at least one liquid extractant is introduced into said absorption column at an entry point located above the entry point of said gaseous feed stream;

(2) withdrawing a gaseous overhead product stream in which the concentration of ethylene is less than in said gaseous feed stream, wherein said gaseous overhead product stream is withdrawn at an exit point located in said absorption column above the entry point of said at least one liquid extractant;

(3) withdrawing a gaseous side product stream in which the concentration of ethylene is higher than in said gaseous feed stream, wherein said gaseous side product stream is withdrawn at an exit point located in said absorption column below the entry point of said gaseous feed stream; and (4) withdrawing a liquid bottoms stream comprising said at least one liquid extractant, at an exit point located in said absorption column below the exit point of said gaseous product stream.

2. A process in accordance with claim 1 wherein said at least one liquid extractant is a solution of at least one copper(I) salt of an alkanesulfonic acid containing 4–20 carbon atoms per molecule which is dissolved in at least one hydrocarbon solvent.

3. A process in accordance with claim 1, wherein said absorption column contains about 30–50 trays at a spacing of about 1–3 feet between trays.

4. A process in accordance with claim 1, wherein the temperature in the upper portion of said absorption column is about 50°–200° F., the temperature in the lower portion of said absorption column is about 200°–400° F., and the pressure in said absorption column is about 5–30 psig.

5. A process in accordance with claim 1, wherein said gaseous side product stream is cooled so as to condense vaporized extractant solvent contained therein.

6. A process in accordance with claim 1, wherein said gaseous feed is a catalytic cracker off-gas.

7. A process in accordance with claim 1, wherein said gaseous feed contains about 1–75 volume percent ethylene.

8. A process in accordance with claim 1, wherein said at least one liquid extractant is a solution of at least one copper(I) salt of an aromatic sulfonic acid containing 6–22 carbon atoms per molecule which is dissolved in at least one hydrocarbon solvent.

9. A process in accordance with claim 8, wherein said liquid extractant is a solution of copper(I) p-dodecylbenzenesulfonate in xylene.

10. A process in accordance with claim 9, wherein the concentration of copper(I) p-dodecylbenzenesulfonate in said solution is about 0.05–2 mole/l.

11. A process in accordance with claim 8, wherein the weight ratio of said at least one copper(I) salt of an aromatic sulfonic acid to said gaseous feed is in the range of about 0.02:1 to about 10:1.

* * * * *